United States Patent [19]

Bissinger et al.

[11] 3,959,487

[45] May 25, 1976

[54] CONTROL OF MITES WITH POLYCHLORO PARATHIO PHENOLS

[75] Inventors: William E. Bissinger, Akron; Donald E. Hardies, Wadsworth; Jerome M. Lavanish, Akron, all of Ohio

[73] Assignee: PPG Industries, Inc., Pittsburgh, Pa.

[22] Filed: July 26, 1974

[21] Appl. No.: 492,086

Related U.S. Application Data

[62] Division of Ser. No. 288,220, Sept. 11, 1972, Pat. No. 3,850,609, which is a division of Ser. No. 766,651, Sept. 28, 1970, Pat. No. 3,723,538.

[52] U.S. Cl. ................................................ 424/337
[51] Int. Cl.$^2$ ...................... A01N 9/00; A01N 9/22
[58] Field of Search ............................. 424/257, 337

[56] References Cited
UNITED STATES PATENTS

| | | | |
|---|---|---|---|
| 3,282,979 | 11/1966 | Reifschneider et al. ............ | 260/465 |
| 3,850,609 | 11/1974 | Bissinger et al. ..................... | 71/98 |

Primary Examiner—Norman A. Drezin
Assistant Examiner—D. W. Robinson
Attorney, Agent, or Firm—Robert J. Grassi; Mark Levin; George D. Morris

[57] ABSTRACT

Chlorinated (alkylthio)phenols, chlorinated (alkenylthio)phenols, and chlorinated (cycloalkylthio)phenols are described which are useful as miticides. These phenols often possess herbicidal, insecticidal, and/or fungicidal properties. Examples of these compounds are 2,3,5,6-tetrachloro-4-(methylthio)phenol and 2,3,6-trichloro-4-(methylthio)phenol.

5 Claims, No Drawings

CONTROL OF MITES WITH POLYCHLORO PARATHIO PHENOLS

This is a division of application Ser. No. 288,220, filed Sept. 11, 1972, now U.S. Pat. No. 3,850,609 which is a division of application Ser. No. 766,651, filed Sept. 28, 1970 now U.S. Pat. No. 3,723,538 issued Mar. 20, 1973.

In accordance with this invention, there are provided phenols which are effective as miticides and which also often possess herbicidal, insecticidal, and/or fungicidal properties.

Phenols here contemplated may be represented by the formula:

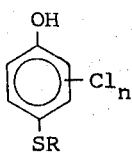

wherein
n is 3 or 4; and
R is lower alkyl, lower alkenyl, or lower cycloalkyl. Subclasses within the scope of the above formula are trichloro-4-(alkylthio)phenol, tetrachloro-4-(alkylthio)phenol, trichloro-4-(alkenylthio)phenol, tetrachloro-4-(alkenylthio)phenol, tetrachloro-4-(alkynylthio)phenol, and tetrachloro-4-(cycloalkylthio)phenol. The trichloro-4-(alkylthio)phenols and the tetrachloro-4-(alkylthio)phenols are preferred.

When R in the above formula is lower alkyl, it usually contains from 1 to 8 carbon atoms. It may be either straight or branched. Most often R is methyl or ethyl. Methyl is preferred.

When R is lower alkenyl, it generally contains from 3 to 8 carbon atoms. Allyl is most often used.

The 2-propynyl group is preferred.

When R is lower cycloalkyl, it typically contains from 3 to 8 carbon atoms. Most often it contains 5 to 8 carbon atoms. Cyclohexyl is preferred.

When the value of n is 3 in the above formula, the chlorine atoms may be arranged in either the 2,3,6-positions or the 2,3,5-positions. The former arrangement is preferred.

An important class falling within the generic invention is represented by the formula:

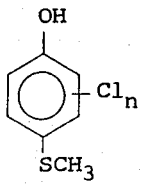

wherein the value of n is 3 or 4. The members of this class are 2,3,5-trichloro-4-(methylthio)phenol, 2,3,6-trichloro-4-(methylthio)phenol, and 2,3,5,6-tetrachloro-4-(methylthio)phenol.

Compounds which exemplify the phenols of the invention are:
2,3,5-trichloro-4-(methylthio)phenol
2,3,5-trichloro-4-(ethylthio)phenol
2,3,5-trichloro-4-(propylthio)phenol
2,3,5-trichloro-4-(isopropylthio)phenol
2,3,5-trichloro-4-(butylthio)phenol
2,3,5-trichloro-4-(sec-butylthio)phenol
2,3,5-trichloro-4-(isobutylthio)phenol
2,3,5-trichloro-4-(tert-butylthio)phenol
2,3,5-trichloro-4-(pentylthio)phenol
2,3,5-trichloro-4-(2-methylbutylthio)phenol
2,3,5-trichloro-4-(hexylthio)phenol
2,3,5-trichloro-4-(1,2-dimethylbutylthio)phenol
2,3,5-trichloro-4-(1-ethyl-2-methylpropylthio)phenol
2,3,5-trichloro-4-(heptylthio)phenol
2,3,5-trichloro-4-(4-methylhexylthio)phenol
2,3,5-trichloro-4-(2,2,3-trimethylbutylthio)phenol
2,3,5-trichloro-4-(1-ethyl-2,2-dimethylthio)phenol
2,3,5-trichloro-4-(1,1-diethylpropylthio)phenol
2,3,5-trichloro-4-(octylthio)phenol
2,3,5-trichloro-4-(3-methylheptylthio)phenol
2,3,5-trichloro-4-(5,5-dimethylhexylthio)phenol
2,3,5-trichloro-4-(1,3,3-trimethylpentylthio)phenol
2,3,5-trichloro-4-(2-methyl-3-ethylpentylthio)phenol
2,3,5-trichloro-4-(2,2,3,3-tetramethylbutylthio)phenol
2,3,5-trichloro-4-(allylthio)phenol
2,3,5-trichloro-4-(3-pentenylthio)phenol
2,3,5-trichloro-4-(cyclopropylthio)phenol
2,3,5-trichloro-4-(cyclopentylthio)phenol
2,3,5-trichloro-4-(cyclohexylthio)phenol
2,3,5-trichloro-4-(cycloheptylthio)phenol
2,3,5-trichloro-4-(cyclooctylthio)phenol
2,3,6-trichloro-4-(methylthio)phenol
2,3,6-trichloro-4-(ethylthio)phenol
2,3,6-trichloro-4-(propylthio)phenol
2,3,6-trichloro-4-(isopropylthio)phenol
2,3,6-trichloro-4-(butylthio)phenol
2,3,6-trichloro-4-(sec-butylthio)phenol
2,3,6-trichloro-4-(isobutylthio)phenol
2,3,6-trichloro-4-(tert-butylthio)phenol
2,3,6-trichloro-4-(pentylthio)phenol
2,3,6-trichloro-4-(1,2-dimethylpropylthio)phenol
2,3,6-trichloro-4-(hexylthio)phenol
2,3,6-trichloro-4-(4-methylpentylthio)phenol
2,3,6-trichloro-4-(1,3-dimethylbutylthio)phenol
2,3,6-trichloro-4-(2-ethylbutylthio)phenol
2,3,6-trichloro-4-(heptylthio)phenol
2,3,6-trichloro-4-(5-methylhexylthio)phenol
2,3,6-trichloro-4-(2,2-dimethylpentylthio)phenol
2,3,6-trichloro-4-(1,2,2-trimethylbutylthio)phenol
2,3,6-trichloro-4-(1,2,3-trimethylbutylthio)phenol
2,3,6-trichloro-4-(1-ethyl-2,2-dimethylpropylthio)phenol
2,3,6-trichloro-4-(1,2-diethylpropylthio)phenol
2,3,6-trichloro-4-(octylthio)phenol
2,3,6-trichloro-4-(2-methylheptylthio)phenol
2,3,6-trichloro-4-(1,4-dimethylhexylthio)phenol
2,3,6-trichloro-4-(2,2,3-trimethylpentylthio)phenol
2,3,6-trichloro-4-(2-ethyl-2-methylpentylthio)phenol
2,3,6-trichloro-4-(1,2,2,3-tetramethylbutylthio)phenol
2,3,6-trichloro-4-(2,2-diethylbutylthio)phenol
2,3,6-trichloro-4-(1-isopropyl-2-methylbutylthio)phenol
2,3,6-trichloro-4-(allylthio)phenol
2,3,6-trichloro-4-(2-pentenylthio)phenol
2,3,6-trichloro-4-(3-hexenylthio)phenol
2,3,6-trichloro-4-(cyclopropylthio)phenol
2,3,6-trichloro-4-(cyclobutylthio)phenol
2,3,6-trichloro-4-(cyclopentylthio)phenol 2,3,6-trichloro-4-(cyclohexylthio)phenol
2,3,6-trichloro-4-(cycloheptylthio)phenol
2,3,6-trichloro-4-(cyclooctylthio)phenol
2,3,5,6-tetrachloro-4-(methylthio)phenol
2,3,5,6-tetrachloro-4-(ethylthio)phenol
2,3,5,6-tetrachloro-4-(propylthio)phenol
2,3,5,6-tetrachloro-4-(isopropylthio)phenol
2,3,5,6-tetrachloro-4-(butylthio)phenol
2,3,5,6-tetrachloro-4-(sec-butylthio)phenol
2,3,5,6-tetrachloro-4-(isobutylthio)phenol
2,3,5,6-tetrachloro-4-(tert-butylthio)phenol
2,3,5,6-tetrachloro-4-(pentylthio)phenol
2,3,5,6-tetrachloro-4-(2-methylbutylthio)phenol
2,3,5,6-tetrachloro-4-(2,2-dimethylpropylthio)-phenol
2,3,5,6-tetrachloro-4-(hexylthio)phenol
2,3,5,6-tetrachloro-4-(3-methylpentylthio)phenol
2,3,5,6-tetrachloro-4-(1,2-dimethylbutylthio)phenol
2,3,5,6-tetrachloro-4-(2,3-dimethylbutylthio)phenol
2,3,5,6-tetrachloro-4-(2-ethylbutylthio)phenol
2,3,5,6-tetrachloro-4-(1-ethyl-2-methylpropylthio)-phenol
2,3,5,6-tetrachloro-4-(heptylthio)phenol
2,3,5,6-tetrachloro-4-(3-methylhexylthio)phenol
2,3,5,6-tetrachloro-4-(1,4-dimethylpentylthio)-phenol
2,3,5,6-tetrachloro-4-(2,2-dimethylpentylthio)-phenol
2,3,5,6-tetrachloro-4-(4,4-dimethylpentylthio)-phenol
2,3,5,6-tetrachloro-4-(2,2,3-trimethylbutylthio)-phenol
2,3,5,6-tetrachloro-4-(1,2,3-trimethylbutylthio)-phenol
2,3,5,6-tetrachloro-4-(1-ethyl-3-methylbutylthio)-phenol
2,3,5,6-tetrachloro-4-(1,2-diethylpropylthio)phenol
2,3,5,6-tetrachloro-4-(octylthio)phenol
2,3,5,6-tetrachloro-4-(1-methylheptylthio)phenol
2,3,5,6-tetrachloro-4-(3-methylheptylthio)phenol
2,3,5,6-tetrachloro-4-(1,2-dimethylhexylthio)phenol
2,3,5,6-tetrachloro-4-(2,3-dimethylhexylthio)phenol
2,3,5,6-tetrachloro-4-(2,4-dimethylhexylthio)phenol
2,3,5,6-tetrachloro-4-(1,2,4-trimethylpentylthio)-phenol
2,3,5,6-tetrachloro-4-(2,2,4-trimethylpentylthio)-phenol
2,3,5,6-tetrachloro-4-(2,4,4-trimethylpentylthio)-phenol
2,3,5,6-tetrachloro-4-(2,3,4-trimethylpentylthio)-phenol
2,3,5,6-tetrachloro-4-(3-ethyl-3-methylpentylthio)-phenol
2,3,5,6-tetrachloro-4-(2,2,3,3-tetramethylbutylthio)-phenol
2,3,5,6-tetrachloro-4-(1,2,2,3-tetramethylbutylthio)-phenol
2,3,5,6-tetrachloro-4-(1-ethyl-2,2-dimethylbutylthio)phenol
2,3,5,6-tetrachloro-4-(1,2-diethylbutylthio)phenol
2,3,5,6-tetrachloro-4-(2,2-diethylbutylthio)phenol
2,3,5,6-tetrachloro-4-(1-propyl-2-methylbutylthio)-phenol
2,3,5,6-tetrachloro-4-(1-isopropyl-2-methylbutylthio)phenol
2,3,5,6-tetrachloro-4-(1-isopropyl-2-methylpropylthio)phenol
2,3,5,6-tetrachloro-4-(allylthio)phenol
2,3,5,6-tetrachloro-4-(2-pentenylthio)phenol
2,3,5,6-tetrachloro-4-(3-pentenylthio)phenol
2,3,5,6-tetrachloro-4-(3-hexenylthio)phenol
2,3,5,6-tetrachloro-4-(4-hexenylthio)phenol
2,3,5,6-tetrachloro-4-(cyclopropylthio)phenol
2,3,5,6-tetrachloro-4-(cyclobutylthio)phenol
2,3,5,6-tetrachloro-4-(cyclopentylthio)phenol
2,3,5,6-tetrachloro-4-(cyclohexylthio)phenol
2,3,5,6-tetrachloro-4-(cycloheptylthio)phenol
2,3,5,6-tetrachloro-4-(cyclooctylthio)phenol These phenols may be prepared by the reaction, in the presence of a base, of the appropriately chlorine substituted thiocyanatophenol and an alcohol of the formula ROH wherein R is lower alkyl, lower alkenyl, or lower cycloalkyl.

Another method of preparation may be achieved by the reaction, in the presence of a base, of the appropriately chlorine substituted thiocyanatophenol and an organic halide of the formula RX wherein R is lower alkyl, lower alkenyl, or lower cycloalkyl and X is a halogen, usually chlorine, bromine, or iodine.

The chlorine substituted thiocyanatophenol starting material may be prepared by reacting (1) the appropriately chlorine substituted phenol having an unsubstituted para-site with (2) ammonium thiocyanate or an alkali metal thiocyanate and (3) an oxidizing agent such as chlorine or bromine.

Reactions similar to the above are shown in U.S. Pat. Nos. 3,231,623; 3,246,039; 3,274,257; 3,282,979; 3,303,206; and 3,303,209.

The phenols of this invention may be prepared by the hydrolysis of a compound represented by the structural formula

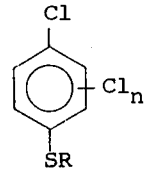

wherein $n$ is 3 or 4 and R is as hereinbefore defined, in the presence of a solvent and at least one base selected from the group consisting of alkali metal hydroxide and alkaline earth metal hydroxide. Sodium hydroxide or potassium hydroxide is most often used. Potassium hydroxide is preferred. Exemplary solvents include the alcohols having from 1 to 10 carbon atoms. The preferred solvents are the tertiary alcohols having from 4 to 10 carbon atoms. Examples of these solvents are methyl alcohol, ethyl alcohol, isopropyl alcohol, tert-butyl alcohol, 1-methylamyl alcohol, tert-amyl alcohol, normal hexyl alcohol, isohexyl alcohol, 2-ethylhexyl alcohol, 1,1-diethylpropyl alcohol, normal decyl alcohol, 1,1-diethyl-3-methylamyl alcohol. Tertiary amyl alcohol or tertiary butyl alcohol is preferred. Mixtures of solvents and/or bases are within contemplation. In a preferred embodiment R is methyl. Hydrolysis is typically carried out at a temperature ranging from about 30°C. to about 200°C. although other temperatures can be used. Most often the temperature is in the range of 80°C. to 150°C. The reaction is ordinarily carried out at atmospheric pressure although greater or lesser pressures may be used if desired. The reaction progresses satisfactorily when the reaction mixture is heated to reflux, usually at atmospheric pressure.

Preparation of the contemplated phenols is illustrated by Examples I–IV.

EXAMPLE I

A 300 ml. two-necked flask is equipped with a magnetic stirrer, thermometer, and dropping funnel. The flask is immersed in a wet ice bath and charged with 100 ml. of methyl alcohol, 6.0 g. of 2,3,5,6-tetrachlorophenol, and 22 g. of potassium thiocyanate. To this solution at 0°C.–5°C. a solution of 4.3 ml. of bromine in 25 ml. of methyl alcohol (saturated with sodium bromide) is added dropwise over a period of 1.5 hours. During the addition a precipitate forms and the mixture becomes quite thick. After an additional 2 hours, the reaction mixture is poured into 400 ml. of water. The aqueous mixture is extracted once with 150 ml. of diethyl ether and three times with 100 ml. portions of diethyl ether. The combined ether extract is dried over sodium sulfite overnight at 0°C. It is filtered and stripped yielding 7.0 g. of light yellow solid. This solid is dissolved in about 40 ml. of hot benzene, filtered while hot, and cooled to give 4.9 g. of light yellow 2,3,5,6-tetrachloro-4-thiocyanatophenol, $\nu_{max}^{mull}$ 2175 cm$^{-1}$. On taking a melting point of this product, it starts to melt at 165°C., then darkens and resolidifies above 185°C. The product is analyzed for carbon, hydrogen, nitrogen, and chlorine. The results expressed in per cent by weight are shown in Table 1.

TABLE 1

Analysis of 2,3,5,6-tetrachloro-4-thiocyanatophenol

|  | C | H | N | Cl |
|---|---|---|---|---|
| Calculated for C$_7$HCl$_4$NOS | 29.1 | 0.35 | 4.85 | 49.2 |
| Found | 28.96 | 0.42 | 4.86 | 48.62 |

A 50 ml. flask is charged with 4.2 g. of 2,3,5,6-tetrachloro-4-thiocyanatophenol, 2,2 g. of methyl iodide, and 20 ml. of methanol. A solution of 3.0 g. of 85 per cent potassium hydroxide in 10 ml. of water is added dropwise with stirring over a period of 70 minutes. After stirring at room temperature for 2 hours, the mixture is stripped to dryness on a rotary film evaporator. The residue is dissolved in 20 ml. of water. This solution is poured into a mixture of 10 ml. of concentrated hydrochloric acid and 25 g. of ice. The white precipitate which forms is separated from the bulk of the liquid by filtration and dried. The residue weighs 3.8 grams. Recrystallization from a mixture of normal hexane and benzene gives 2.4 g. of pale yellow crystals having a melting point range of 121°C. to 123.5°C. The product is 2,3,5,6-tetrachloro-4-(methylthio)phenol and may be depicted as having the structural formula:

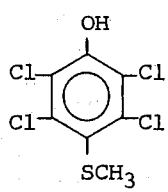

EXAMPLE II

A 500 ml. three-necked flask is equipped with a mechanical stirrer, a thermometer, and a dropping funnel. The flask is immersed in a wet ice bath and charged with 200 ml. methyl alcohol, 20.0 g. of 2,3,6-trichlorophenol, and 35.0 g. of potassium thiocyanate. To the stirred mixture at 4°C.–8°C. a solution of 11.0 ml. of bromine in 40 ml. of methyl alcohol (saturated with sodium bromide) is added dropwise over a period of one hour. The mixture is stirred an additional half hour and then poured into 1000 ml. of water. The aqueous mixture is extracted once with 150 ml. of diethyl ether and three times with 100 ml. portions of diethyl ether. The combined ether extract is dried over sodium sulfite, filtered, and stripped on a rotary evaporator thereby yielding 28 g. of yellow solid. Gas chromatographic analysis of methylene chloride solutions of the yellow solid show the yellow solid to be about 60 per cent 2,3,6-trichloro-4-thiocyanatophenol and the rest 2,3,6-trichlorophenol. The yellow solid is redissolved in 30 ml. of methyl alcohol along with 40 g. of potassium thiocyanate. To the stirred mixture at 3°C.–8°C. a solution of 11.0 ml. of bromine in 40 ml. of methyl alcohol (saturated with sodium bromide) is added dropwise over a period of 40 minutes. After stirring an additional hour, the reaction mixture is extracted once with 150 ml. of diethyl ether and three times with 100 ml. portions of diethyl ether. The combined ether extract is dried over sodium sulfite, filtered, and stripped on a rotary evaporator thereby yielding 21.0 g. of yellow solid. Gas chromatographic analysis of this yellow solid shows it to be more than 90 per cent 2,3,6-trichloro-4-thiocyanatophenol. This yellow solid is dissolved in hot benzene, filtered while hot to remove a dark red semi-solid, and cooled to give 14.4 g. of light yellow 2,3,6-trichloro-4-thiocyanatophenol, melting point range 128°C.–129°C., $\nu_{max}^{mull}$ 2179 cm$^{-1}$.

A 100 ml. flask is charged with 4.1 g. of 2,3,6-trichloro-4-thiocyanatophenol, 2,3 g. of methyl iodide, and 30 ml. of methanol. A magnetic stirring bar is added and the flask is fitted with a pressure equalized addition funnel charged with 2.7 g. of potassium hydroxide in 15 ml. of water. The potassium hydroxide solution is added dropwise over a period of 30 minutes with stirring. After 2 hours the mixture is concentrated under vacuum until about 25 ml. of solution remained. This is poured into a mixture of 20 ml. of concentrated hydrochloric acid and 25 g. of ice. The tan solid which separates is filtered, washed with two 25 ml. portions of water, and dried to give 3.8 g. of tan powder. Recrystallization from a mixture of normal hexane and chloroform gives, after filtration and drying 1.5 g. of tan needles having a melting point range of 128°C.–129°C., $\nu_{max}^{mull}$ 3380 cm$^{-1}$ (broad, OH) and nuclear magnetic resonance signals at 2.49$\delta$ (singlet, 3H) and 7.22 $\delta$ (singlet, 1H). The spectra are consistent with 2,3,6-trichloro-4-(methylthio)phenol. The product is analyzed for carbon, hydrogen, and chlorine. The results expressed in per cent by weight are shown in Table 2.

TABLE 2

Analysis of 2,3,6-trichloro-4-(methylthio)phenol

|  | C | H | Cl |
|---|---|---|---|
| Calculated for C$_7$H$_5$Cl$_3$OS | 34.5 | 2.0 | 43.7 |
| Found | 33.8 | 2.0 | 44.5 |

The product may be depicted as having the structural formula:

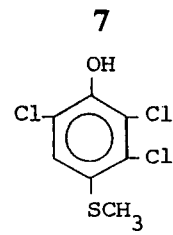

EXAMPLE III

The compound 2,3,5-trichloro-4-thiocyanatophenol is prepared in a manner similar to that of Example II using 2,3,5-trichlorophenol in lieu of 2,3,6-trichlorophenol. The compound 2,3,5-trichloro-4-(methylthio)-phenol is prepared in a manner similar to that of Example II using 4.1 g. of 2,3,5-trichloro-4-thiocyanatophenol in place of 4.1 g. of 2,3,6-trichloro-4-thiocyanatophenol.

The product may be depicted as having the structural formula:

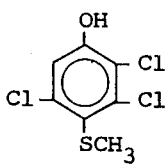

Example IV illustrates another way in which 2,3,5,6-tetrachloro-4-(methylthio)phenol may be prepared.

EXAMPLE IV

A 100 ml. three-necked flask is fitted with a mechanical stirrer, a thermometer, and a reflux condenser. The flask is charged with 8.9 g. of pentachlorothioanisole (from pentachlorothiophenol and methyl sulfate according to the method of Kulka, *Journal of Organic Chemistry*, Vol. 24 (February, 1959), pp. 235–237, 6.7 g. of potassium hydroxide and 50 ml. of tertiary butyl alcohol and heated to reflux for 17.5 hours. After cooling, the reaction mixture is poured into a round-bottomed flask. The solvent is then stripped on a rotary film evaporator until the solid residue appears dry. The addition of 50 ml. of water gives a cloudy solution which is washed with two 25 ml. portions of benzene. The aqueous solution is heated on a steam bath until enough residual benzene is driven off for the solution to become clear. The solution is allowed to cool. Concentrated hydrochloric acid is then added until no further cloudiness appeared. An oil separates which is dissolved in benzene. The benzene solution is dried and concentrated on a rotary film evaporator to give 4.7 g. of waxy brown crystals. They are dissolved in a refluxing mixture of normal hexane and benzene, filtered while still hot, and allowed to cool. The crystals which form are filtered and dried. They weigh 1.8 g. and have a melting point range of 108°C.–116°C. A second recrystallization from a mixture of normal hexane and chloroform gives 1.1 g. of tan crystals with a melting point range of 119°C.–120.5°C., $\nu_{max.}^{mull}$ 3420 cm$^{-1}$ (broad, OH) and a single nuclear magnetic resonance signal at 2.38δ. The spectral data are consistent with 2,3,5,6-tetrachloro-4-(methylthio)phenol. The product is analyzed for carbon, hydrogen, and chlorine. The results expressed in per cent by weight are shown in Table 3.

TABLE 3

Analysis of 2,3,5,6-Tetrachloro-4-(methylthio)-phenol

|  | C | H | Cl |
|---|---|---|---|
| Calculated for $C_7H_4Cl_4OS$ | 30.3 | 1.5 | 51.2 |
| Found | 29.3 | 1.5 | 51.9 |

The product may be depicted as having the structural formula:

In general, the phenols of this invention may be used to kill or retard development of mites.

In one embodiment the phenol is applied directly to the mites by bringing a miticidal amount of a compound into mutual contact with the mites. In another embodiment the phenol is applied to regions where mites are likely to be found in order to kill the mites present or to preclude mite populations from becoming established.

Usually formulations containing from about 5 to about 2,000 parts per million by weight (ppm) of the phenol compound are applied. Typical formulations contain from about 10 to about 1,000 ppm. Often formulations containing from about 10 to about 100 ppm are used.

The type of formulation used may vary. Solutions and suspensions of the phenol are effective. The usual method of applying solutions or suspensions is to drench the area of application. Sprays, showers, mists, and dips may be used for this purpose. When some of the more active phenols are used, particularly at the higher concentrations, a complete drenching is not necessary. Mists are often used where a drench is not desired.

The phenol formulations of the invention may also be applied in the form of a powder or dust. These powders or dusts may contain diluents such as, for example, aluminum silicate, bentonite, calcium carbonate, calcium silicate, diatomaceous silica, hydrated lime, pulverized limestone, montmorillonite, pulverized phosphate rock, silica, talc, or vermiculite.

The concentration of the phenol compound in the formulation and the total amount applied will vary depending upon the particular phenol being employed and the particular mite being confronted. Other facts such as season of the year, environmental conditions, and stage of mite development all have their effect.

The following specific embodiments illustrate, by way of example, the basic principles of the present invention.

EXAMPLE V

Potted horticultural bean plants (*Phaseolus vulgaris* L.) at growth stage when primary leaves are approximately 1 inch long are infested with two-spotted spider mites (*Tetranychus urticae*) 24 hours prior to treatment, insuring establishment of adults and deposition of eggs at the time of treatment.

A stock acetone emulsion is prepared having the following composition by weight: 99.75 per cent acetone, 0.20 per cent sorbitan trioleate (Span 85), and 0.05 per cent sorbitan monooleate polyoxyalkylene derivative (Tween 80). Test compound is dissolved in a portion of the stock acetone emulsion. Deionized water is added to yield a concentrated test solution containing about 10 per cent acetone, 0.020 per cent Span 85, and 0.0050 per cent Tween 80. The amount of test compound dissolved in the stock acetone emulsion is such that when diluted with deionized water the concentrated test solution has the highest concentration (usually 1,000 ppm) of test compound used in the tests. Solutions which are prepared by diluting the concentrated test solution with a mixture of deionized water and stock acetone emulsion, which mixture contains about 10 per cent acetone, 0.020 per cent Span 85, and 0.0050 per cent Tween 80. Thus, all test solutions always contain about 10 per cent acetone, 0.020 per cent Span 85, and 0.0050 per cent Tween 80, irrespective of the concentration of test compound.

Infested host plants are dipped into agitated solutions of the test compound, allowed to air dry, provided with a subterranean water source, and held for observation. Three test plants are used for each unit of treatment.

Initial mortality is determined 48 to 72 hours after treatment by removing and observing one leaf from each plant. Final observations of mortality, ovicidal action, and residual toxicity to emerging nymphs are made 7 days after treatment by removal and observation of the second primary leaf. The observed results are reported in terms of Per Cent Mortality. Table 4 reports observed results where the test compound is 2,3,5,6-tetrachloro-4-(methylthio)phenol.

TABLE 4

Miticidal Effectiveness of 2,3,5,6-Tetrachloro-4-(methylthio)phenol Against Two-Spotted Spider Mite (*Tetranychus urticae*)

| Concentration ppm | Per Cent Mortality Initial | Ovicidal | Residual |
|---|---|---|---|
| 1,000 | 100 | 90 | 100 |
| 500 | 100 | Trace | 0 |
| 250 | 100 | 0 | 0 |
| 100 | 75,72 | 0 | 0 |
| 50 | 53 | — | — |
| 25 | 37 | — | — |

EXAMPLE VI

The procedure of Example V is repeated using 2,3,6-trichloro-4-(methylthio)phenol as the test compound. The results are shown in Table 5.

TABLE 5

Miticidal Effectiveness of 2,3,6-Trichloro-4-(methylthio)phenol Against Two-Spotted Spider Mite (*Tetranychus urticae*)

| Concentration ppm | Per Cent Mortality Initial | Ovicidal | Residual |
|---|---|---|---|
| 1,000 | 100 | 0 | 100 |
| 500 | 100 | 0 | 100 |
| 250 | 100 | 0 | 95 |
| 100 | 96 | 0 | Trace |
| 50 | 80 | — | — |
| 25 | 21 | — | — |
| 10 | 15 | — | — |

Many of the phenols of the present invention possess properties which make them useful as phytocides, as for example, herbicides. Weeds may be killed by applying to the soil in the vicinity of the weeds a phytocidal amount of the phenol. Weeds may also be killed by bringing the weeds and a phytocidal amount of the phenol into mutual contact, as for example, by applying the phenol to the weeds. In another embodiment the phenol is applied to the soil where weeds are likely to be found in order to preclude weeds from becoming established.

The formulations used as phytocides are similar in all material respects to those described above for miticidal purposes. The concentration of the phenol in the formulation and the total amount applied will vary depending upon the particular phenol being employed and the particular weed being confronted. Other factors such as season of the year, environmental conditions, and stage of weed development all have their effect. Exemplary application rates are from about 0.1 to about 100 pounds per acre. Usually the rate will range from about 0.1 to about 20 pounds per acre. Rates of from about 0.5 to about 10 pounds per acre are most often used.

In Examples VII through XIII the following procedure was used: For pre-emergence testing, appropriate weed species are seeded in individual disposable 3-inch square containers containing about 2 inches of soil. After spraying directly on the seeded soil surface, a small amount of sand, usually about ⅛ to ¼ inch in depth, is applied to cover the seeds.

For post-emergence testing, appropriate weed species are seeded by growth-time requirement schedules in individual disposable 3 inch square containers containing about 2 inches of soil, watered as required, and maintained under greenhouse conditions. When all weeds have reached suitable growth development, generally first true leaf stage, plants appropriate to pertaining test requirements are selected for uniformity of growth and development. One container of each weed, averaging up to 50 plants per individual container, is then placed on a carrying tray for treatment.

When possible, the test compounds are formulated in a solvent mixture of 90% acetone, 8% methanol, and 2% dimethylformamide by volume. Insoluble compounds are formulated as wettable powders and diluted with water and wetting agent before application.

Each carrying tray of pre-emergence and/or post emergence containers, placed on a conveyor belt having a linear speed of 1.5 miles per hour, trips a microswitch which, in turn, activates a solenoid valve and releases the compound under test. The compound under test is discharged as sprays at a rate of 50 gallons per acre. Containers used for pre-emergence testing are then watered. Containers for both pre-emergence and post-emergence testing are then removed to the greenhouse and held for observation.

Pre-emergence and post-emergence treatments are observed daily for interim response, final observations usually being made 14 days after treatment. Any treatments inducing significant response are held beyond the 14-day observation period until such responses can be confirmed. Each result is reported as an Injury Rating which is represented as follows: 0 — no visible effect; 1, 2, 3 — slight injury, plant usually recovered with little or no reduction in top growth; 4, 5, or 6 — moderate injury, plants usually recovered but with reduced top growth, 7, 8, or 9 — severe injury, plants usually did not recover; 10 — all plants killed. Deviations from the above procedure, if any, are reported with the data.

EXAMPLE VII

Test Compound: 2,3,5,6-Tetrachloro-4-(methylthio)phenol

Pre-Emergence Observations made 16 days after application

Post-Emergence Observations made 13 days after application

| Test Plant | Pre-Emergence 5 lb./A | Post-Emergence 5 lb./A |
|---|---|---|
| Yellow Nutsedge (*Cyperus esculentus* L.) | 5 | 8 |
| Wild Oats (*Avena fatua* L.) | 2 | 9 |
| Jimsonweed (*Datura stramonium* L.) | 0 | 10 |
| Velvetleaf (*Abutilon theophrasti* Medic.) | 2 | 10 |
| Johnsongrass (*Sorghum halepense* Pers.) | 4 | 8 |
| Lambsquarter (*Chenopodium album* L.) | 10 | — |
| Mustard (*Brassica kaber* L. C. Wheeler Var. *pinnatifida* L. C. Wheeler) | 8 | 10 |
| Yellow Foxtail (*Setaria glauca* Beauv.) | 2 | 9 |
| Barnyardgrass (*Echinochloa crusgalli* Beauv.) | 2 | 7 |
| Crabgrass (*Digitaria sanguinalis* Scop.) | 8 | 8 |
| Buckwheat (*Polygonum convolvulus* L.) | 2 | 10 |
| Morning Glory (mixture of *Ipomoea purpurea* Roth and *Ipomoea hederacea* Jacq.) | 5 | 9 |
| Red Kidney Bean (*Phaseolus vulgaris* L.) | | |
| Primary Leaf Stage | — | 10 |
| Trifoliate Leaf Stage | — | 10 |
| Untreated Controls | Normal | Normal |

EXAMPLE VIII

Test Compound: 2,3,5,6-Tetrachloro-4-(methylthio)phenol

Observations made 21 days after application

| Test Plant | Pre-Emergence 5 lb./A |
|---|---|
| Yellow Nutsedge (*Cyperus esculentus* L.) | 4 |
| Wild Oats (*Avena fatua* L.) | 0 |
| Jimsonweed (*Datura stramonium* L.) | 0 |
| Velvetleaf (*Abutilon theophrasti* Medic.) | 0 |
| Johnsongrass (*Sorghum halepense* Pers.) | 4 |
| Lambsquarter (*Chenopodium album* L.) | 6 |
| Mustard (*Brassica kaber* L. C. Wheeler Var. *pinnatifida* L. C. Wheeler) | 8 |
| Yellow Foxtail (*Setaria glauca* Beauv.) | 3 |
| Barnyardgrass (*Echinochloa crusgalli* Beauv.) | 2 |
| Crabgrass (*Digitaria sanguinalis* Scop.) | 8 |
| Buckwheat (*Polygonum convolvulus* L.) | 2 |
| Morning Glory (mixture of *Ipomoea purpurea* Roth and *Ipomoea hederacea* Jacq.) | 5 |
| Untreated Controls | Normal |

EXAMPLE IX

Test Compound: 2,3,5,6-Tetrachloro-4-(methylthio)phenol

Observations made 14 days after application

| Test Plant | Post-Emergence 5 lb/A | 2 lb/A | 1 lb/A |
|---|---|---|---|
| Yellow Nutsedge (*Cyperus esculentus* L.) | 7 | 2 | 0 |
| Wild Oats (*Avena fatua* L.) | 10 | 7 | 3 |
| Jimsonweed (*Datura stramonium* L.) | 10 | 10 | 10 |
| Velvetleaf (*Abutilon theophrasti* Medic.) | 10 | 10 | 10 |
| Johnsongrass (*Sorghum halepense* Pers.) | 3 | 2 | 1 |
| Mustard (*Brassica kaber* L. C. Wheeler Var. *pinnatifida* L. C. Wheeler) | 10 | 10 | 9 |
| Yellow Foxtail (*Setaria glauca* Beauv.) | 10 | 7 | 6 |
| Barnyardgrass (*Echinochloa crusgalli* Beauv.) | 8 | 7 | 6 |
| Crabgrass (*Digitaria sanguinalis* Scop.) | 10 | 9 | 7 |
| Buckwheat (*Polygonum convolvulus* L.) | 10 | 10 | 8 |
| Morning Glory (mixture of *Ipomoea purpurea* Roth and *Ipomoea hederacea* Jacq.) | 10 | 10 | 9 |
| Red Kidney Bean (*Phaseolus vulgaris* L.) | | | |
| Primary Leaf Stage | 2 | 2 | 2 |
| Trifoliate Leaf Stage | 9 | 5 | 2 |
| Untreated Controls | Normal | Normal | Normal |

EXAMPLE X

Test Compound: 2,3,6-Trichloro-4-(methylthio)phenol

Pre-Emergence Observations made 16 days after application

Post-Emergence Observations made 13 days after application

| Test Plant | Pre-Emergence 5 lb./A | Post-Emergence 5 lb./A |
|---|---|---|
| Yellow Nutsedge (*Cyperus esculentus* L.) | 0 | 8 |
| Wild Oats (*Avena fatua* L.) | 0 | 8 |
| Jimsonweed (*Datura stramonium* L.) | 5 | 10 |
| Johnsongrass (*Sorghum halepense* Pers.) | 4 | 1 |
| Lambsquarter (*Chenopodium album* L.) | 0 | — |
| Mustard (*Brassica kaber* L. C. Wheeler Var. *pinnatifida* L. C. Wheeler) | 6 | 10 |
| Velvetleaf (*Abutilon theophrasti* Medic.) | 2 | 10 |
| Yellow Foxtail (*Setaria glauca* Beauv.) | 2 | 2 |
| Barnyardgrass (*Echinochloa crusgalli* Beauv.) | 2 | 5 |
| Crabgrass (*Digitaria sanguinalis* Scop.) | 7 | 8 |
| Buckwheat (*Polygonum convolvulus* L.) | 0 | 10 |
| Morning Glory (mixture of *Ipomoea purpurea* Roth and *Ipomoea hederacea* Jacq.) | 0 | 8 |
| Red Kidney Bean (*Phaseolus vulgaris* L.) | | |
|   Primary Leaf Stage | — | 10 |
|   Trifoliate Leaf Stage | — | 10 |
| Untreated Controls | Normal | Normal |

EXAMPLE XI

Test Compound: 2,3,6-Trichloro-4-(methylthio)-phenol

Observations made 21 days after application

| Test Plant | Pre-Emergence 5 lb./A |
|---|---|
| Yellow Nutsedge (*Cyperus esculentus* L.) | 0 |
| Wild Oats (*Avena fatua* L.) | 1 |
| Jimsonweed (*Datura stramonium* L.) | 6 |
| Velvetleaf (*Abutilon theophrasti* Medic.) | 0 |
| Johnsongrass (*Sorghum halepense* Pers.) | 4 |
| Lambsquarter (*Chenopodium album* L.) | 0 |
| Mustard (*Brassica kaber* L. C. Wheeler Var. *pinnatifida* L. C. Wheeler) | 7 |
| Yellow Foxtail (*Setaria glauca* Beauv.) | 0 |
| Barnyardgrass (*Echinochloa crusgalli* Beauv.) | 2 |
| Crabgrass (*Digitaria sanguinalis* Scop.) | 4 |
| Buckwheat (*Polygonum convolvulus* L.) | 0 |
| Morning Glory (mixture of *Ipomoea purpurea* Roth and *Ipomoea hederacea* Jacq.) | 0 |
| Untreated Controls | Normal |

EXAMPLE XII

Test Compound: 2,3,5,6-Tetrachloro-4-(methylthio)phenol

Observations made 14 days after application

| Test Plant | Post-Emergence 2 lb/A | 0.5 lb/A |
|---|---|---|
| Sugar Beet (*Beta vulgaris* L.) | 10 | 8 |
| Corn (*Zea mays* L.) | 2 | 1 |
| Oats (*Avena sativa* L.) | 2 | 3 |
| Red Clover (*Trifolium pratense* L.) | 10 | 9 |
| Soybean (*Glycine max* [L.] Merr.) | 5 | 5 |
| Cotton (*Gossypium hirsutum* L.) | 5 | 1 |
| Wheat (*Triticum aestivum* L.) | 5 | 2 |
| Peanut (*Arachis hypogaea* L.) | 2 | 1 |
| Rice (*Oryza sativa* L.) | 6 | 3 |
| Kentucky Bluegrass (*Poa pratensis* L.) | 1 | 1 |
| Alfalfa (*Medicago sativa* L.) | 10 | 9 |
| Flax (*Linum ulsitatissimum* L.) | 4 | 2 |
| Pigweed (*Amaranthus retroflexus* L.) | 5 | 2 |
| Wild Oats (*Avena fatua* L.) | 10 | 7 |
| Russian Thistle (*Salsola kali* L. Var *Tenuifolia* Tausch) (from seed) | 10 | 10 |
| Horsenettle (*Solanum carolinense* L.)(from seed) | 7 | 5 |
| Purple Nutsedge (*Cyperus rotundus* L.) (from tubers) | 0 | 0 |
| Peppergrass (*Lepidum campestre* [L.] R. Br.) | 8 | 5 |
| Chickweed (*Stellaria media* [L.] Cyrillo) | 9 | 7 |
| Cocklebur (*Xanthium pennsylvanicum* Wallr.) | 10 | 4 |
| Giant Foxtail (*Setaria faberii* Herrm.) | 1 | 0 |
| Johnsongrass (*Sorghum halepense* [L.] Pers.) (from rhizomes) | 0 | 0 |
| Hedge Bindweed (*Convolvulus Sepium* L.) (from rhizomes) | 7 | 4 |
| Quackgrass (*Agropyron repens* [L.] Beauv.) (from rhizomes) | 0 | 0 |

EXAMPLE XIII

Test Compound: 2,3,6-Trichloro-4-(methylthio)-phenol

Observations made 14 days after application

| Test Plant | Post-Emergence 2 lb/A | 0.5 lb/A |
|---|---|---|
| Sugar Beet (*Beta vulgaris* L.) | 5 | 4 |
| Corn (*Zea mays* L.) | 4 | 4 |
| Oats (*Avena sativa* L.) | 8 | 7 |

| Test Plant | Post-Emergence | |
|---|---|---|
| | 2 lb/A | 0.5 lb/A |
| Red Clover (*Trifolium pratense* L.) | 9 | 8 |
| Soybean (*Glycine max* [L.] Merr.) | 6 | 5 |
| Cotton (*Gossypium hirsutum* L.) | 3 | 2 |
| Wheat (*Triticum aestivum* L.) | 5 | 4 |
| Peanut (*Arachis hypogaea* L.) | 2 | 2 |
| Rice (*Oryza sativa* L.) | 7 | 5 |
| Kentucky Bluegrass (*Poa pratensis* L.) | 1 | 1 |
| Alfalfa (*Medicago sativa* L.) | 9 | 9 |
| Flax (*Linum ulsitatissimum* L.) | 5 | 5 |
| Pigweed (*Amaranthus retroflexus* L.) | 5 | 4 |
| Wild Oats (*Avena fatua* L.) | 10 | 3 |
| Russian Thistle (*Salsola kali* L. Var. *Tenuifolia* Tausch) (from seed) | 10 | 3 |
| Horsenettle (*Solanum carolinense* L.) (from seed) | 6 | 4 |
| Purple Nutsedge (*Cyperus rotundus* L.) (from tubers) | 0 | 0 |
| Peppergrass (*Lepidum campestre* [L.] R. Br.) | 7 | 4 |
| Chickweed (*Stellaria media* [L.] Cyrillo) | 7 | 4 |
| Cocklebur (*Xanthium pennsylvanicum* Wallr) | 4 | 2 |
| Giant Foxtail (*Setaria faberii* Herrm.) | 2 | 1 |
| Johnsongrass (*Sorghum halepense* [L.] Pers.) (from rhizomes) | 0 | 0 |
| Hedge Bindweed (*Convolvulus Sepium* L.) (from rhizomes) | 10 | 5 |
| Quackgrass (*Agropyron repens* [L.] Beauv.) (from rhizomes) | 5 | 0 |

While the invention has been described with reference to certain illustrative embodiments, it is not intended that it shall be limited thereby except insofar as appears in the accompanying claims.

We claim:

1. A method of killing mites which comprises applying to the mites a miticidal amount of a compound represented by the structural formula:

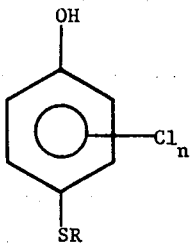

wherein:
$n$ is 3 or 4; and

R is selected from the group consisting of lower alkyl containing from 1 to 8 carbon atoms, lower alkenyl containing from 3 to 8 carbon atoms, and lower cycloalkyl containing from 3 to 8 carbon atoms.

2. The method of claim 1 wherein R is lower alkyl containing from 1 to 8 carbon atoms.

3. The method of claim 1 wherein the compound is represented by the structural formula:

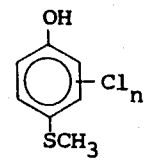

wherein $n$ is 3 to 4.

4. The method of claim 3 wherein the compound is 2,3,6-trichloro-4-(methylthio)phenol.

5. The method of claim 3 wherein the compound is 2,3,5,6-tetrachloro-4-(methylthio)phenol.

* * * * *